United States Patent
Comeau et al.

(10) Patent No.: US 6,657,274 B2
(45) Date of Patent: Dec. 2, 2003

(54) APPARATUS FOR CONTROLLING A HIGH VOLTAGE CIRCUIT USING A LOW VOLTAGE CIRCUIT

(75) Inventors: Alain R. Comeau, Carlsbad, CA (US); Jonas Per Ludvig Weiland, Del Mar, CA (US)

(73) Assignee: Microsemi Corporation, Irvine, CA (US)

(*) Notice: Subject to any disclaimer, the term of this patent is extended or adjusted under 35 U.S.C. 154(b) by 24 days.

(21) Appl. No.: 09/976,700

(22) Filed: Oct. 11, 2001

(65) Prior Publication Data

US 2003/0071322 A1 Apr. 17, 2003

(51) Int. Cl.[7] .............................................. H01L 29/00
(52) U.S. Cl. ...................................................... 257/500
(58) Field of Search ................... 29/577, 578; 257/368; 438/238, 286, 275

(56) References Cited

U.S. PATENT DOCUMENTS

| | | | |
|---|---|---|---|
| 4,475,280 A | * | 10/1984 | Ragonese et al. ........... 438/324 |
| 5,543,740 A | | 8/1996 | Wong |
| 5,591,209 A | | 1/1997 | Kroll |
| 5,622,886 A | * | 4/1997 | Allum et al. ................ 438/238 |
| 5,693,952 A | | 12/1997 | Cox |
| 5,805,436 A | | 9/1998 | Lin |
| 5,875,103 A | | 2/1999 | Bhagwat et al. |
| 5,963,066 A | | 10/1999 | Fukunaga |
| 6,144,539 A | | 11/2000 | Konopka et al. |
| 6,160,304 A | | 12/2000 | Ludikhuize |
| 6,370,050 B1 | | 4/2002 | Peng et al. |

\* cited by examiner

Primary Examiner—David Nelms
Assistant Examiner—Mai-Huong Tran
(74) Attorney, Agent, or Firm—Jackson Walker LLP; Michael Cameron, Esq.; Robert Klinger, Esq.

(57) ABSTRACT

Disclosed is a capacitively coupled bridge circuit for using a low-voltage circuit to operate a high-voltage circuit. The invention maintains isolation between the high- and low-voltage sections by using a capacitor. Also disclosed is the use of the invention in an inplantable cardiac defibrillator.

10 Claims, 3 Drawing Sheets

APPARATUS FOR CONTROLLING A HIGH VOLTAGE CIRCUIT USING A LOW VOLTAGE CIRCUIT

TECHNICAL FIELD

This invention relates to a power supply circuit, and more specifically, to a capacitively coupled bridge circuit for using a low-voltage circuit section to control a high-voltage circuit section while maintaining isolation between the high- and low-voltage sections.

BACKGROUND OF THE INVENTION

In many electronic systems a low voltage source is often needed to control a corresponding high voltage source. One such need, for example, is commonly found in a device known as an Implantable Cardiac Defibrillator (ICD), in which a high voltage pulse is controlled by a low voltage integrated circuit (IC). In many instances, delivery of the higher voltage is accomplished by way of a non-complementary high voltage switching matrix encompassing a bridge configuration. This switching element frequently employs N-channel Metal-Oxide Semiconductor Field Effect Transistors (MOSFETs), or Insulated Gate Bipolar Transistors (IGBTs), or Silicon Controlled Rectifiers (SCR) depending on the design specifications.

In order to enhance the overall performance of a system that involves low-to-high voltage transfer, isolation between both the voltage-generating and voltage-delivering functions is crucial. In a bridge or a switching matrix configuration having N-Channel MOSFETs or IGBTs, for instance, the transistor gate voltage needs to be higher than, or independent of, the switching voltage. The low voltage section of the system cannot, therefore, be used to provide the gate voltage directly. Therefore, an alternative method of maintaining and transferring the necessary gate voltage must be implemented.

In the art, two known methods are used to achieve level shifting and input-to-output isolation. The first involves using a transformer in combination with a full-wave bridge rectifier circuit; the other involves circuits using opto-couplers.

Although transformers combined with diode rectifiers may be adequate for shifting voltage levels, design considerations limit their use in certain situations. First, transformers are bulky, and hence, are unsuitable in certain applications where minimizing the three-dimensional space of the device is critical, such as in an ICD. Similarly, transformers are discrete devices, and thus, cannot be incorporated in a CMOS integrated circuit (IC).

Opto-couplers, on the other hand, suffer from the same size impediments as isolation transformers. Moreover, in dual- or multi-channel design applications, opto-couplers are susceptible to signal distortion and cross talk.

Accordingly, a power supply that delivers a high power output controlled by low power input while simultaneously capacitively isolating the two sources would be advantageous. Such a device would also have the advantage of being readily integrated into standard CMOS IC production processes. The performance characteristics and small size of IC embodiments of such a device would be particularly advantageous for use in small-size applications such ICD's.

SUMMARY OF THE INVENTION

The invention provides a power supply with integral control circuit for providing a low-voltage control signal with capacitive coupling to a high-voltage section having an output for powering a load. The power supply is adapted to operate the high-voltage section in response to a signal from the low-voltage section.

According to one aspect of the invention, the integral control circuit and capacitive coupling are implemented as a single IC.

According to another aspect of the invention, the integral control circuit is implemented as a full bridge rectifier driver circuit.

Embodiments of the invention disclosed include implantable cardiac defibrillator circuits where a bridge section capacitively couples the low voltage section to the high voltage section.

The invention provides several technical advantages over the prior art. The capacitive coupling used by the invention is smaller and less expensive to implement than isolation devices used in the arts. The remainder of the accompanying bridge circuit provides advantages in terms of operational characteristics, manufacturing techniques, and size. The invention is particularly advantageous for use in applications concurrently demanding fast response, a high degree of portability, and reliable isolation of high- and low-voltage circuit components. One example of such an application is an implantable cardiac defibrillator. Further advantages will become apparent to those skilled in the arts upon review of the following description, figures and claims.

BRIEF DESCRIPTION OF THE DRAWINGS

For a better understanding of the invention including its features, advantages and specific embodiments, reference is made to the following detailed description along with accompanying drawings in which.

References in the detailed description correspond to like references in the figures unless otherwise noted. The figures are not to scale and some features may appear minimized or exaggerated to illustrate the invention.

DETAILED DESCRIPTION

Figure 1:
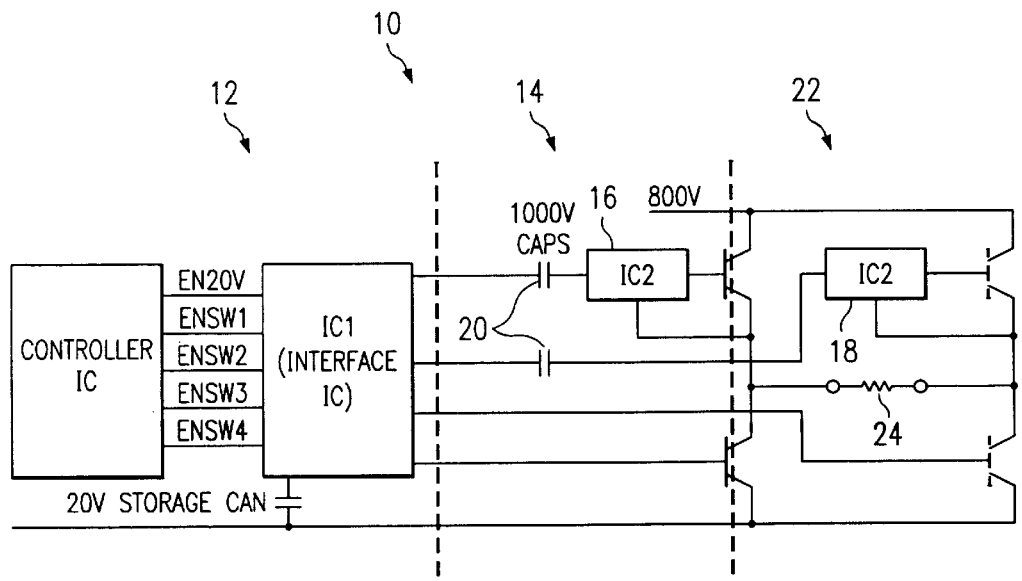
FIG. 1 is a block diagram showing an example of the components of the invention.

In FIG. 1 is shown a block diagram of an example of the invention in the form of a full image driver circuit 10. A low voltage section 12 provides a relatively low voltage control signal to a bridge section 14. Preferably, the control signal is an oscillating signal within a frequency range ($F_{osc}$) of about 1 MHz–10 MHz, at about 6V–24V, although other generating frequencies may be employed. As shown in FIG. 1, the bridge section 14 may have a high portion 16 and a low portion 18, which are functionally and physically mirror-images of one another, providing a full bridge driver circuit 10. The bridge section 14 may be contained on a single IC. Isolation capacitors 20 are used to couple the low voltage section 12 with the bridge portion 14. The isolation capacitors 20 are preferably included on an IC with the bridge portion 14, although they may be alternatively external, or included on an IC with the low voltage section 12. The isolation capacitors 20 are selected to withstand the maximum peak voltage of the high voltage portion 22. The high voltage portion 22 is coupled to a load 24. In the preferred embodiment, the high voltage section 22 supplies about 800V–1000V to the load 24.

In general, the bridge portion 14 of the invention 10 provides an isolating and controlling connection between the low voltage section 12 and the high voltage section 22. The invention 10 is designed to provide electrical isolation through the use of an isolation capacitor 20. The components and configuration of the bridge portion 14, further shown and described below, provide a circuit 10 with desirable rise- and fall-time ($t_{rise}$ and $T_{fall}$) characteristics as well as size and integration advantages at the invention.

Figure 2:
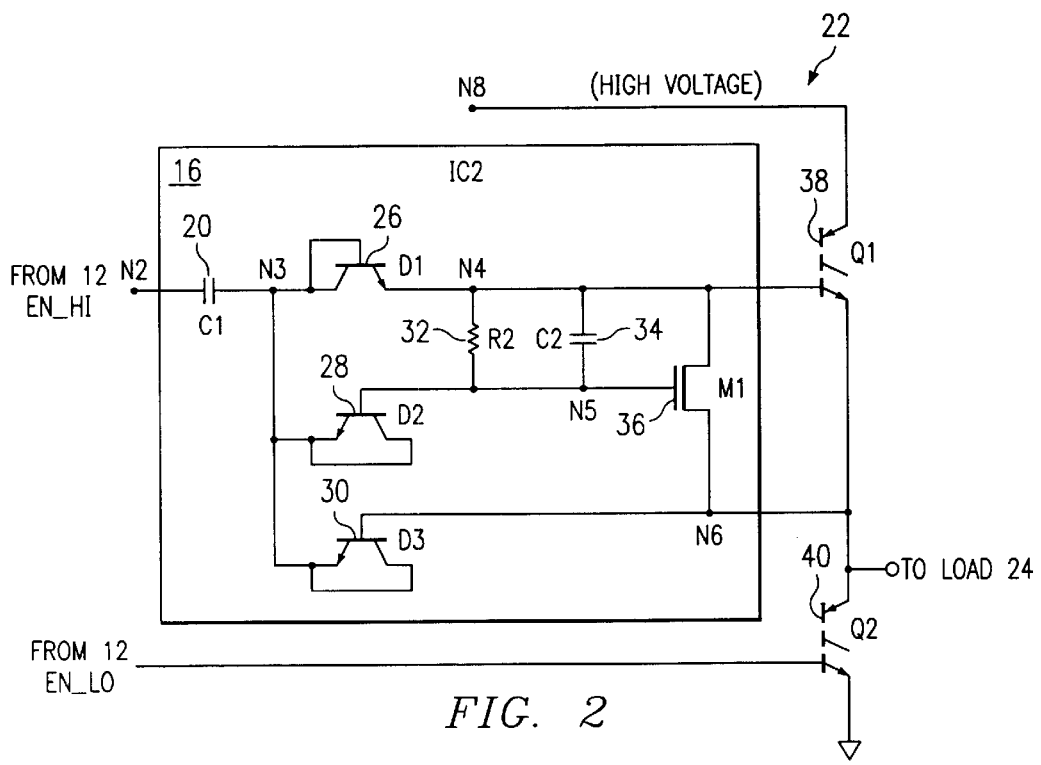
FIG. 2 is a circuit diagram showing a close-up schematic view of the bridge section of the invention of FIG. 1.

Now referring to FIG. 2, a close up view of a bridge section 14 of the invention is shown. In the preferred embodiment, the isolation capacitor 20 is included on an IC also containing the bridge section 14. The isolation capacitor 20 is coupled to the low voltage section 12 on one side and to the remainder of the bridge section 14 at node N3. In the preferred embodiment, the substrate is used as the input (node N3) to facilitate implementation of the high voltage isolation capacitor 20 directly in the CMOS process, if desired, without any modifications to other components, e.g., D1, D2, D3, and M1. For the isolation capacitor 20, reliability at high voltage is required since this device effectively provides the high voltage isolation between the low voltage section 12 and the high voltage section 22. The capability of the isolation capacitor 20 to withstand high voltages is preferably achieved by adjusting the thickness of dielectric between the top metal plate and the substrate, as well as by usual high voltage layout rules for surrounding circuitry and guard rings. An isolation capacitor 20 in the range of 50–100 pF able to withstand about 800V–1000V is presently preferred.

A forward-biased diode D1 26 is connected to node N3 as are first and second reverse-biased diodes D2 28 and D3 30. At the opposing terminal of the forward-biased diode D1 26, at node N4, a resistor R2 32 and capacitor C2 34 pair join the opposing terminal of the first reverse-biased diode D2 28 at node N5. Capacitor C2 34 must be fairly well isolated from the input signal (node N3) present on the substrate to prevent the low voltage section 12 input signal from bypassing the first reverse-biased diode D2 28. This is preferably achieved by using a double polysilicon capacitor.

The parasitic capacitance between the substrate and the bottom polysilicon plate is on the order of 10% of the inter-poly capacitance. In addition to being reasonably isolated from the substrate, the use of a double polysilicon capacitor allows the choice of connecting the bottom plate to node N4 or to node N5. Transistor M1 36 itself provides a parasitic capacitance between N4 and N3. It is, therefore, desirable to place additional parasitic capacitance, preferably 5–20 pF, between node N5 and node N3. Thus, a configuration where the capacitor C2 34 bottom plate is tied to node N5 is preferred. Resistor R2 32 optimized along with C2 34, to provide a time constant ($T_{rc}$) appropriate for the oscillation frequency ($F_{osc}$) range used. Typically $T_{rc}$ is 3 to 10 times longer than the inverse minimum frequency used (e.g., 1 MHz to 10 MHz). Parasitic capacitance coupling to node N3 is reduced when R2 32 is made of polysilicon and furthermore if the polysilicon has a higher sheet resistance reducing the size, and therefore parasitic capacitance, resulting in a resistor of smaller area. A resistor R2 32 of about 500 KΩ to 3 MΩ is presently preferred, as it provides acceptably low parasitic capacitance.

A transistor M1 36, preferably an NMOSFET, has its source connected to node N4 and its gate connected to node N5. Also connected to node N4 is a power transistor Q1 38. It can be seen that at node N6 the drain of the NMOSFET transistor M1 36 is connected to the remaining terminal of the second reverse-biased diode 30. Node N6 is ultimately connected to the load 24 through a second transistor Q2 40 of the high voltage section 22.

With continued reference to FIG. 2, the operation of the invention can be understood by following an electrical path through the bridge portion 14 beginning with the low voltage section 12 output signal passing through the isolation capacitor 20 at node N2. Those skilled in the arts will readily perceive that the mirror image bridge 14 (FIG. 1) functions in a like manner with the clock cycles reversed, forming a full bridge rectifier circuit 10. The invention may be practiced in full or half bridge configurations.

If the control signal output by the low voltage Section 12 is off (EN_HI is off), node N2 is at ground. Capacitor C2 34 couples any voltage on node N4 to the gate of transistor M1 36, node N5. As voltage between nodes N4 and N6 (N5 is approximately the same voltage as on N4) rises above the threshold voltage of M1 36, M1 36 will begin conducting and short the gate of Q1 38 to the source (N4 to N6), effectively limiting the node N4–N6 voltage difference to about 1V. Preferably M1 36 has a threshold voltage of about 0.7V and Q1 38 has a threshold voltage between 2.5 and 5.5 Volt. This difference in turn-on voltage effectively means that Q1 38 remains off in the event of a voltage spike on node N8 while the control signal is low.

To provide protection for fast rising surges in the high voltage section 22, a normally-off NMOSFET is preferred for M1 36. If a positive spike were to arise on the high voltage drain of Q1 38, there would be a risk that the parasitic collector-gate capacitance (N8 to N4) could feed a substantial portion of this peak to the Q1 38 gate, possibly turning on Q1 38 at an inappropriate time. The configuration shown in FIG. 2 provides inherent protection against this undesirable turn-on. During normal OFF state operation, any transient attempt to charge the Q1 38 gate results in transistor M1 36 turning on before the gate of Q1 38 reaches its threshold voltage. This is because the threshold of transistor M1 36 is only about 0.7V while that of transistor Q1 38 is about 2.5 to 5.5V. Transitor M1 36 effectively acts as an AC coupled forward diode in this configuration limiting the voltage across nodes N4–N6 to about 1.0V.

If the low voltage section 12 control signal is on (EN_HI on), typically the control signal oscillates at $F_{osc}$=10 MHz–20 MHz), and there is a charge transfer from node N3 to node N4 via the forward-biased diode 26. This charge is stored in the parasitic gate-source capacitance of Q1 38. When N3 goes negative with respect to N4, there is a charge transfer to the isolation capacitor 20 from N6 and from N5 via N3. Node N5 then slowly discharges towards N4 with a time constant ($T_{rc}$) determined by the value of the resistor R2 32 and by the total capacitance at node N5. The total capacitance is typically dominated by C2 34. The time constant determined by R2 32 and C2 34 is preferably made substantially longer than the inverse frequency of the incoming AC signal on N2 so as to maintain the voltage on N5 as close to that of N6 as possible, ensuring that M1 36 stays in an OFF-state. Under the condition $T_{rc} \gg 1/F_{osc}$, the gate-emitter voltage (N4–N6) of Q1 38 increases and eventually reaches its turn-on voltage. The gate-emitter capacitance of Q1 38, diode D3 30 and diode D1 26 ensures that node N4 follows node N6 to the high voltage. Once M1 36 has reached its turn-on voltage, the circuit 14 acts as an AC source follower, thereby pushing N6 up by the peak-to-peak value, the AC voltage (minus a few diode forward drops) at node N2 for every clock cycle. Hence, shorter rise time is achieved with high node N2 AC voltage and high frequency.

Once N6 has reached a value close to that of node N8 (high voltage section 22), then the AC current from node N2 fails to further push up node N4. This node is then charged with the full swing of AC voltage (N2). Note that at this point voltage at node N4 exceeds voltage at node N8. Thus, circuit 10 turns on Q1 38 from a capacitively isolated low voltage source 12. While in this state, little current is consumed by the bridge section 14 as C2 20 and the gate of Q1 38 are fully charged.

When the oscillator stops (setting EN_HI to ground), node N5 discharges towards node N4. When N5–N6 voltage goes beyond the M1 36 threshold voltage, M1 36 turns on shorting N4 and N6 which, in turn, leak the charge from the gate of Q1 38 and turns it off.

Figure 3:
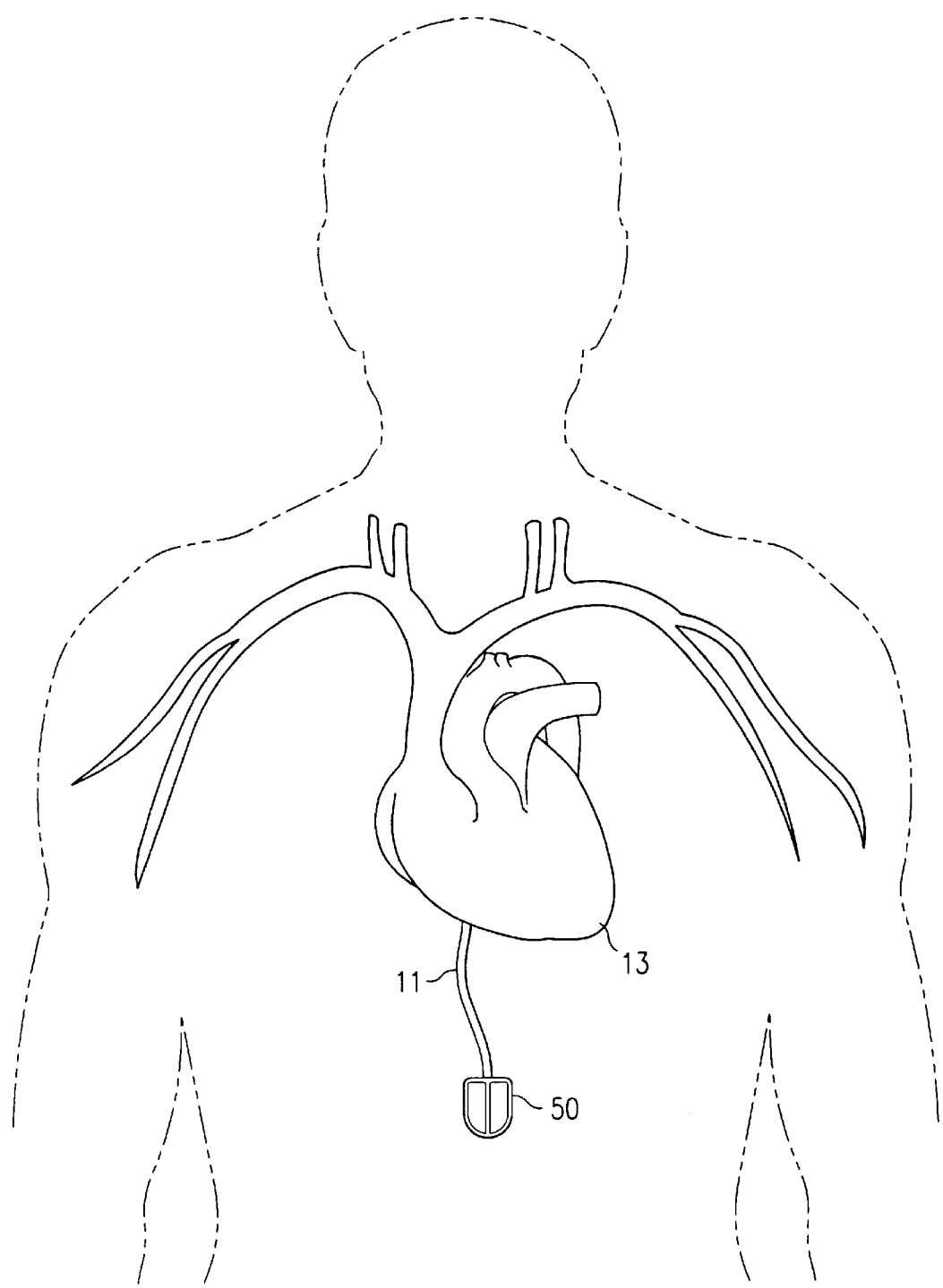
FIG. 3 is a block diagram showing an example of an implantable cardiac defibrillator embodiment of the invention.

FIG. 3 depicts the invention embodied in an implantable cardiac defibrillator, denoted generally as 50, in an epicardial implantation. Those skilled in the arts will appreciate that the invention may be used with various types of atrial, ventrical, or other defibrillators using various implantation configurations. The device 50 is connected to leads 11 positioned inside the heart 13 used to deliver electrical impulses, sense the cardiac rhythm, or pace the heart 13.

To implement the bridge circuit 14 and the high voltage isolation capacitor 20 on the same integrated circuit, certain characteristics are desirable for the components. FIGS. 4–8 show cross-sections of preferred embodiments of these bridge circuit 14 components for use with the invention.[1]

[1]This next page may be a bit rough. I'll need help to reconcile the conflicts between the two sets of figures and the text of the disclosure.

Figure 4:
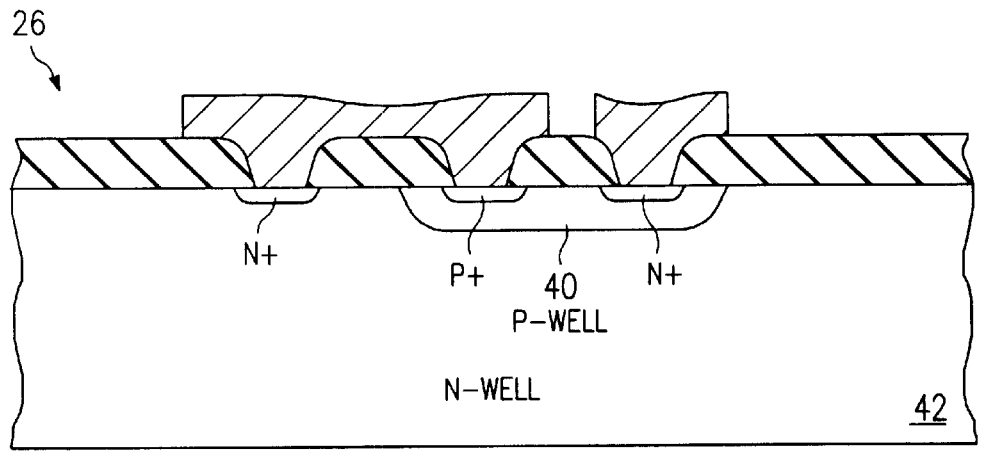
FIG. 4 is a cross sectional side view of a preferred embodiment of diode D1 of FIG. 2.

Referring to FIG. 4, the forward-biased diode D1 26 must effectively reverse block the full voltage swing at node N2. In most CMOS processes, P–/N– well diodes provide high breakdown voltage. Unfortunately, these diodes (P– well/N–substrate) are prohibitively slow for high-speed applications, such as cardiac defibrillators. Therefore, it is preferred to use a N+ /P-well bipolar transistor in a diode configuration. This provides a high voltage diode D1 26 capable of operating at high speeds yet adaptable to standard CMOS fabrication processes.

In addition to blocking reverse voltage, diode D1 26 must be fast enough to switch the AC control signal from node N2. A problem which can arise with normal simple diodes P+/N– for example, is that the injected forward current, holes in the N– material, is available only after the minority carriers have recombined, resulting in a delay. This delay makes such devices relatively slow. Faster switching is achieved if a bipolar connection is used. The minority carrier flow is only through the base 40 and the current is readily available once it reaches the collector (N– substrate). These devices are, therefore, much faster than the simple bipolar diodes. Proper polarity for the diode is obtained when the substrate (P–)[2] is connected to the N–/well (and the P– base). Alternatively, diode device D1 26 may be made using Schottky junction metal-semiconductors.

[2]Do we mean N–?

Figure 5:
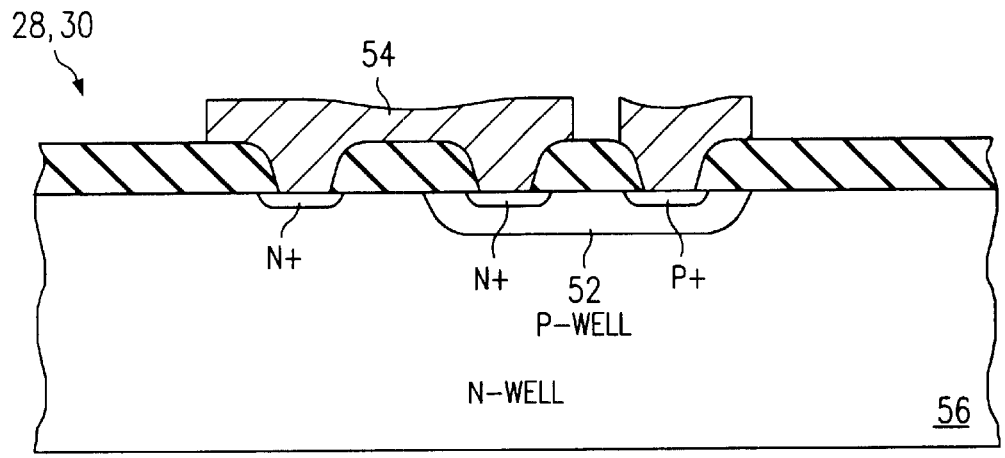
FIG. 5 is a cross sectional side view of a preferred embodiment of diodes D2 and D3 of FIG. 2.

Referring now to FIG. 5, reverse-biased diodes D2 28 and D3 30 have the same voltage breakdown and speed requirements as diode D1 26, but they must function when connected with the opposite polarity. Adequate performance may be maintained by connecting the P– well 52 to the emitter (N+) 54, resulting in a base-emitter diode with the emitter 54 tied to the well node 52. The base 53 is then tied to the N-substrate 56. Diodes made using minimum design rules provide little parasitic capacitance while having enough forward drive capability and enough speed. For D2 28 and D3 30, it is preferred to substitute P– well/N–substrate transistors connected with the base-collector common (N+).

Figure 6:
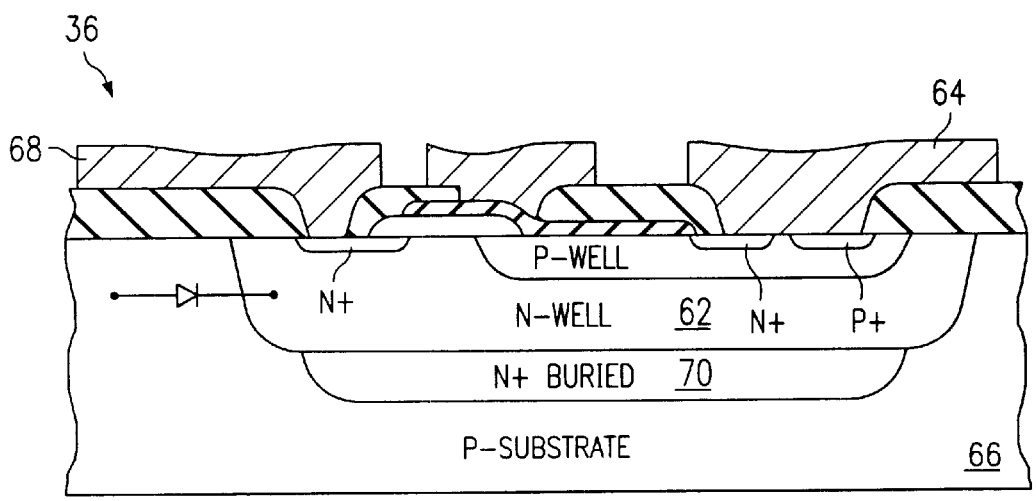
FIG. 6 is a cross sectional side view of a preferred embodiment of transitor M1 of FIG. 2.

FIG. 6 depicts a preferred embodiment of transitor M1 36. M1 36 is a moderate-voltage NMOSFET (–20V) made in a well 62 to isolate it from the input low voltage control signal. The preferred configuration allows the source junction 64 to be isolated from the substrate 66, reducing the risk of latch-up. Such a configuration lets a parasitic diode (D1 26) come between the drain 68 and the substrate 66, which is in parallel with D1 26. However, D1 26 is a fast-switching diode compared to the well diode, and in AC, D1 26 dominates current flow. The drawback from the parasitic drain diode D3 30 at M1 36 is added junction capacitance, which reduces reverse voltage (AC current) isolation. For this reason, M1 36 is preferably kept small. Since transistor M1 36 is only active during the fall time ($t_{fall}$), it is important to ensure that proper discharge with fast enough drop rate is present. Fast drop rate and fast rise rate are required to prevent the power driving transistor Q1 38 from thermal runaway, which would destroy it. Specification for this minimum rise-fall time should be in line with the requirements of the transistor used for Q1 38. In the preferred embodiment, $t_{rise}$ and $t_{fall}$ are less than about 50 uSec from 1000V. The P– well 68 of M1 36 is tied to the most negative node in the circuit, which is node N6, the Q1 38 emitter (FIG. 2). This node (N6) also corresponds to the source connection 64 of M1 36. A N+ buried layer 70 under the N-well eliminates vertical NPN action when the drain-substrate diode D1 26 is forward biased. Such a configuration creates a collected current at the source 64 and reduces the charge build-up at node N4.

While the invention has been described with regard to specific and illustrative embodiments, this description and the following claims are not intended to be construed in a limiting sense. Various modifications and combinations of the illustrative embodiments as well as other embodiments of the invention will become apparent to persons skilled in the art upon reference to the description and is intended that such variations be encompassed and included within the meaning and scope of the following claims.

We claim:

1. A full bridge rectifier driver circuit comprising:
 a low voltage section for providing a high frequency control signal;
 a high voltage section having an output for powering a load;
 a bridge section capacitively coupling the low voltage section to the high voltage section, the bridge section further comprising a high portion adapted to operate the high voltage section in response to a high signal from the low voltage section and a low portion adapted to operate the high voltage section in response to a low signal from the low voltage section.

2. A full bridge rectifier driver circuit according to claim 1 wherein the bridge section comprises an integrated circuit.

3. A full bridge rectifier driver circuit according to claim 1 wherein the bridge section high portion and bridge section low portion comprise a first and a second integrated circuit.

4. A full bridge rectifier driver circuit according to claim 1 wherein the bridge section comprises an integrated circuit and an external isolation capacitor.

5. A full bridge rectifier driver circuit according to claim 1 wherein the low voltage section further comprises an isolation capacitor.

6. A full bridge rectifier driver circuit according to claim 1 further comprising:
- a first transistor having its base and emitter terminals coupled with the high voltage section for supplying power to the load, and its gate operably coupled to the high portion of the bridge section; and
- a second transistor having its base and emitter terminals coupled with the high voltage section for supplying power to the load, and its gate operably coupled to the low portion of the bridge section.

7. A full bridge rectifier driver circuit according to claim 6 wherein the bridge section high portion and low portion each further comprise:
- an isolation capacitor having one terminal coupled to the low voltage section output;
- a forward-biased diode and first and second reverse-biased diodes coupled to the opposing terminal of the isolation capacitor;
- a resistor and capacitor (RC) pair coupled in parallel with the forward-biased diode and the first reverse-biased diode; and
- an NMOSFET having its gate terminal coupled with the RC and first reverse-biased diode, and its source terminal coupled with the RC pair, forward-biased diode and gate of the first transistor, and its drain terminal coupled with the second reverse-biased diode and base of the first transistor.

8. The full bridge rectifier driver circuit of claim 7 adapted for use with a low voltage section output within a frequency range of approximately 1 MHz–10 MHz.[4]

[4] It would be good to insert the broadest range you can reasonably conceive using.

9. The full bridge rectifier driver circuit of claim 7 wherein the RC pair is selected to exhibit a time constant within a range of approximately three to ten times longer than the minimum frequency used for the low voltage section output.

10. The full bridge rectifier driver circuit of claim 6 wherein the diodes comprise N+ substrate P-well bipolar transistors.

* * * * *